United States Patent [19]

Jones

[11] Patent Number: 4,663,481

[45] Date of Patent: May 5, 1987

[54] PREPARATION OF BROMOACETAMIDES

[76] Inventor: John D. Jones, 57 Keats Rd., Greenmount, Bury BL8 4EP, Lancashire, England

[21] Appl. No.: 673,091

[22] Filed: Nov. 19, 1984

[30] Foreign Application Priority Data

Dec. 7, 1983 [GB] United Kingdom ................. 8332608

[51] Int. Cl.$^4$ .................... C07C 102/08; C07C 103/22
[52] U.S. Cl. ...................................... 564/124; 564/155
[58] Field of Search ................................ 564/124, 155

[56] References Cited

FOREIGN PATENT DOCUMENTS 0059536 9/1982 European Pat. Off. ............ 564/124
0076030 4/1983 European Pat. Off. ............ 564/124

*Primary Examiner*—Charles F. Warren
*Assistant Examiner*—Carolyn S. Greason

[57] ABSTRACT

Bromoacetamides of the formula $ArCONHCH(Br)CONH_2$ are obtained by addition to bromine of a solution of $ArCONHCH_2CN$ in a saturated aliphatic carboxylic acid preferably glacial acetic or propionic acid. This is an improvement in a process described in European Patent Specification No. 0059536 in which the bromine is added to a solution of the cyanomethylbenzamide, enabling consistently high yields (e.g. 75 to 90%) to be obtained.

5 Claims, No Drawings

PREPARATION OF BROMOACETAMIDES

This invention relates to a process for the preparation of certain substituted bromoacetamides which are useful chemical intermediates in the synthesis of fungicidal compounds.

Substituted amide derivatives of the formula (A):

in which $R^1$ is aryl, $X^1$ is O, S or NH and $R^2$ is optionally substituted alkyl or alkenyl when $X^1$ is O or S, or optionally substituted alkanoyl when $X^1$ is NH, and which are proposed for use as herbicides and fungicides, are described in European Patent Specification No. 59536 together with processes for their preparation. One such process involves a sequence of chemical reactions in the following scheme:

Scheme

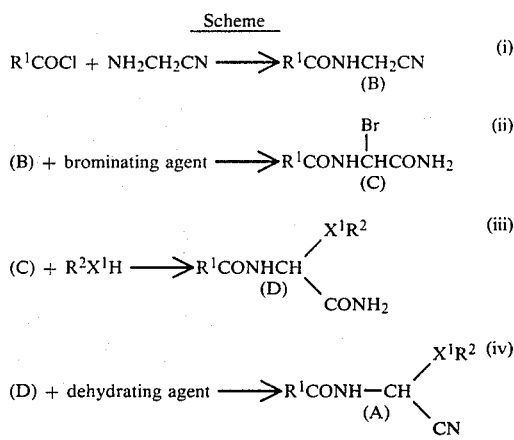

In step (i) of the scheme, an acid chloride $R^1COCl$ is reacted with aminoacetonitrile by a conventional procedure to obtain the compound (B). This is then reacted in step (ii) with a brominating agent (for example bromine in glacial acetic acid) to give the brominated derivative (C). The bromination simultaneously hydrates the cyano group to a carbamoyl group —CONH$_2$ necessitating treatment with a dehydrating agent later. In step (iii), the bromo compound (C) is reacted with an appropriate alcohol, thiol, or amine of formula $R^2X^1H$ to obtain the carbamoyl compound (D) which is then treated with the dehydrating agent in step (iv) to convert it to the corresponding cyano compound (A).

The bromination step (ii) involves the addition of bromine to a solution of the compound (B) in glacial acetic acid. In practice, this has been found to give inconsistent and often low yields of less than 50% of the alpha-bromoamide (C). The present invention is concerned with improving this bromination step.

According to the present invention there is provided a process for the preparation of a substituted alpha-bromoacetamide of the formula (I):

in which Ar is optionally substituted aryl, by reaction of bromine with a compound of the formula (II):

$$ArCONHCH_2CN \quad (II)$$

characterised in that a solution of compound (II) in a saturated aliphatic carboxylic acid is added to bromine.

The compound of formula (II) may be readily obtained by reacting an acid chloride, ArCOCl, with aminoacetonitrile in known manner.

The optionally substituted aryl group Ar may be a phenyl or naphthyl radical. Examples of substituents which may be present include fluorine, chlorine, bromine, iodine, $C_1$-$C_4$ alkoxy, methylenedioxy and ethylenedioxy, $C_1$-$C_4$ alkyl, $C_1$-$C_4$ alkylthio, $C_1$-$C_4$ haloalkyl (e.g. $CF_3$) nitro and cyano. There may be from one to three or more substituents which may be the same or different. When Ar is a substituted phenyl radical the substituents are preferably in the 3, 4 or 5 positions. When a methylenedioxy or ethylenedioxy substituent is present, it is preferably attached to the 3 and 4 positions of the phenyl ring. A halogen substituent (e.g. Cl or Br) may also be present in the 4- or 5-position, or both, in such compounds. The process of the invention is of particular value in the preparation of 4-chlorobenzoylamino-alpha-bromoacetamide and its 4-bromo analogue.

The saturated aliphatic carboxylic acid is preferably a monocarboxylic acid and more preferably has the formula RCOOH in which R is $C_{1-4}$ alkyl. In particular, there is mentioned propionic acid and especially acetic acid.

The amount of carboxylic acid used should be sufficient to dissolve compound (II) but not so much as to slow subsequent reaction with the bromine by overdilution of the reaction medium. When glacial acetic acid is used, the concentration of compound (II) is conveniently from 5 to 7% weight by volume of the acid. In propionic acid, the compound (II) is less soluble and a concentration of about 2% is appropriate.

It is preferred, though not essential, that the bromine itself is in solution in the same or a different saturated aliphatic carboxylic acid when the solution of compound (II) is added to it. A concentration of bromine of 6 to 7% weight by volume of acid is suitable. As an alternative the bromine may be dissolved in an inert solvent, such as dichloromethane.

To ensure complete reaction, one mole of bromine should be used for each mole of compound (II) but no excess is necessary.

The solution of compound (II) is added to the bromine at such a rate as to maintain the temperature of the exothermic reaction within a range of from 10° to 100° C., preferably from 30° to 40° C. Typically, on a 0.01 molar scale, a 6 to 7% glacial acetic acid solution of compound (II) at 35° C. is added dropwise to a 6 to 7% glacial acetic acid solution of bromine over half an hour.

During reaction the product, compound (I), is precipitated as it is formed and towards the end of reaction the bromine solution pales and is finally decolourised. At the end of reaction the mixture is cooled, filtered and the residual product washed with, for example, ether or dichloromethane and dried.

The process of the invention enables consistently high yields, e.g. 75 to 90%, of compound (I) to be obtained compared with a process in which bromine is added to a solution of compound (II).

Compound (I) may then be processed as described in European Patent Specification No. 59536, by reaction with an appropriate alcohol, thiol or amide of the formula $R^3XH$, to form a compound of formula (III):

(III)

This is then treated with a dehydrating agent, such as p-toluenesulphonyl chloride in pyridine, to convert to the compound of formula (IV):

(IV)

which is a useful herbicide or fungicide.

When $R^3XH$ is an alcohol or thiol, $R^3$ is optionally substituted alkyl or alkenyl, for example $C_{1-4}$ alkyl and $C_{3-5}$ alkenyl optionally substituted with halogen, or $C_{1-4}$ alkoxy. When $R^3XH$ is an amide, $R^3$ is optionally substituted alkanoyl, preferably $C_{1-4}$ alkanoyl, for example, formyl, acetyl or propionyl.

The invention is illustrated by the following Examples 1 to 12 in which percentages are by weight.

EXAMPLE 1

Bromination of N-cyanomethyl-4-chlorobenzamide

N-cyanomethyl-4-chlorobenzamide (1.95 g, 0.01 M) dissolved in glacial acetic acid (30 ml) at 35° C. was added dropwise with stirring to a solution of bromine (1.6 g, 0.01 M) in glacial acetic acid (25 ml) over 30 minutes. Towards the end of benzamide addition the bromine solution paled and was finally decolourised. During benzamide addition a precipitate was produced in the reaction flask. At the end of reaction the mixture was cooled to room temperature and filtered. The pale apricot solid residue was washed with diethyl ether and dried. It was identified as 4-chlorobenzoylamino-alpha-bromoacetamide by comparison of its infra red spectrum with that of an authentic sample of the same compounds and its melting point of 185° C. with decomposition. The yield was 2.5 g, 85.8% theory on the chlorobenzamide.

EXAMPLES 2 TO 9

The procedure of Example 1 was repeated in each of Examples 2 to 9. The yields of 4-chlorobenzoylamino-alpha-bromoacetamide obtained are shown in Table 1.

TABLE 1

| Example No. | Yield % |
| --- | --- |
| 2 | 82.3 |
| 3 | 81.0 |
| 4 | 85.8 |
| 5 | 89.2 |
| 6 | 84 |
| 7 | 84 |
| 8 | 82 |
| 9 | 85.8 |

EXAMPLE 10

Bromination of N-cyanomethyl-4-bromobenzamide

The procedure of Example 1 was repeated except that 2.39 g (0.01 M) of N-cyanomethyl-4-bromobenzamide was used instead of the 1.95 g of the 4-chloro analogue. A white solid residue obtained on filtration of the reaction mixture, was washed with dichloromethane, instead of diethylether, and dried. The residue was identified as 4-bromobenzoylamino-alpha-bromoacetamide by comparison of its IR spectrum with that of an authentic sample of the same product and its melting point of 182° C. with decomposition. The yield was 83% theory.

EXAMPLE 11

Bromination of N-cyanomethyl-4-chlorobenzamide in propionic acid

N-Cyanomethyl-4-chlorobenzamide (1.95 g, 0.01 M) was dissolved in propionic acid (100 ml) at 35°–40° C. and added dropwise with stirring to a solution of bromine (1.6 g, 0.01 M) in propionic acid (25 ml) over 30 minutes. Towards the end of benzamide addition the bromine solution paled and finally decolourised. During benzamide addition a precipitate was produced in the reaction flask. At the end of reaction the mixture was cooled to room temperature and filtered. The pale apricot solid residue was washed with dichloromethane and dried giving a yield of 2.2 g; 75.5% theory on the chlorobenzamide.

The IR spectrum of the product was identical to an authentic sample of 4-chlorobenzoylamino-alpha-bromoacetamide and had a melting point of 178° C. with decomposition.

EXAMPLE 12

Bromination of N-cyanomethyl-4-methylbenzamide in acetic acid

N-cyanomethyl-4-methylbenzamide (3.48 g, 0.02 M) was dissolved in glacial acetic acid (60 ml) at 40° C. and added dropwise with stirring to a solution of bromine (3.2 g, 0.02 M) in glacial acetic acid (10 ml) over 30 minutes. Towards the end of methylbenzamide addition the bromine solution paled and was finally decolourised. During methylbenzamide addition a precipitate was produced in the reaction flask. At the end of reaction the mixture was cooled to room temperature and filtered. The pale apricot solid residue was washed with dichloromethane and dried at 70° C. It was identified as 4-methylbenzoylamino-alpha-bromoacetamide by comparison of its IR spectrum with that of an authentic sample of the same product.

Yield=4.35 g 80% theory based on the methylbenzamide starting material.

mp=165° C. with frothing and decomposition.

What I claim is:

1. A process for the preparation of a substituted alpha-bromoacetamide of the formula (I):

(I)

in which Ar is optionally substituted aryl, by reaction of bromine with a compound of the formula (II):

(II)

characterised in that a solution of compound (II) in a saturated aliphatic carboxylic acid is added to bromine.

2. A process according to claim 1 in which Ar is phenyl carrying one or more substituents selected from fluorine, chlorine, bromine, iodine, $C_1$-$C_4$ alkoxy, methylenedioxy and ethylenedioxy, $C_1$-$C_4$ alkyl, $C_1$-$C_4$ alkylthio, $C_1$-$C_4$ haloalkyl, nitro and cyano.

3. A process according to claim 1 in which the carboxylic acid has the formula RCOOH in which R is $C_{1-4}$ alkyl.

4. A process according to claim 1 in which the solution of compound II is added to the bromine at such a rate as to maintain the temperature of the exothermic reaction within a range of from 10° to 100° C.

5. A process according to claim 1 wherein a solution of compound (II) in glacial acetic acid is added to a glacial acetic acid solution of bromine, the solution of compound (II) being added gradually so as to maintain the reaction temperature at between 30° C. and 40° C.

* * * * *